US012599295B2

(12) United States Patent (10) Patent No.: US 12,599,295 B2
Ito (45) Date of Patent: Apr. 14, 2026

(54) CONTROL DEVICE

(71) Applicant: OLYMPUS MEDICAL SYSTEMS CORP., Tokyo (JP)

(72) Inventor: Takeshi Ito, Hino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 5 days.

(21) Appl. No.: 18/748,259

(22) Filed: Jun. 20, 2024

(65) Prior Publication Data

US 2024/0423463 A1 Dec. 26, 2024

Related U.S. Application Data

(60) Provisional application No. 63/522,779, filed on Jun. 23, 2023.

(51) Int. Cl.
| *A61B 1/06* | (2006.01) |
| *H04N 23/11* | (2023.01) |
| *H04N 23/12* | (2023.01) |
| *H04N 23/72* | (2023.01) |
| *H04N 23/74* | (2023.01) |
| *H04N 23/76* | (2023.01) |
| *H04N 23/88* | (2023.01) |

(52) U.S. Cl.
CPC .......... *A61B 1/0638* (2013.01); *A61B 1/0655* (2022.02); *H04N 23/11* (2023.01); *H04N 23/12* (2023.01); *H04N 23/72* (2023.01); *H04N 23/74* (2023.01); *H04N 23/76* (2023.01); *H04N 23/88* (2023.01)

(58) Field of Classification Search
CPC ................ A61B 1/0638; A61B 1/0655; A61B 1/000094; A61B 1/043; H04N 23/11; H04N 23/12; H04N 23/72; H04N 23/74; H04N 23/76; H04N 23/88; H04N 5/265; H04N 23/555; H04N 23/56
See application file for complete search history.

(56) References Cited

U.S. PATENT DOCUMENTS

| 8,790,253 B2* | 7/2014 | Sunagawa ............ A61B 1/0661 |
| | | 600/109 |
| 2011/0071353 A1* | 3/2011 | Ozawa ................. A61B 1/0653 |
| | | 600/109 |

(Continued)

FOREIGN PATENT DOCUMENTS

JP 2012010962 A 1/2012

*Primary Examiner* — Michael Lee
(74) *Attorney, Agent, or Firm* — Scully, Scott, Murphy & Presser, P.C.

(57) ABSTRACT

A control device includes one or more processors including hardware, the one or more processors being configured to: generate a white light image based on a first image signal captured as a result of irradiating a subject with a white light; generate a narrow-band light image based on a second image signal captured as a result of irradiating the subject with a narrow-band light; control a light intensity of the white light to a first value which is determine according to brightness of the white light image and according to a first ratio; and control a light intensity of the narrow-band light to a second value which is determine according to brightness of the narrow-band light image and according to a second ratio that is different than the first ratio.

18 Claims, 14 Drawing Sheets

(56) References Cited

U.S. PATENT DOCUMENTS

| | | | |
|---|---|---|---|
| 2012/0101348 A1* | 4/2012 | Yamaguchi | A61B 1/043 |
| | | | 600/109 |
| 2012/0127293 A1* | 5/2012 | Yamazaki | A61B 1/07 |
| | | | 348/71 |
| 2015/0022647 A1* | 1/2015 | Takei | A61B 1/0655 |
| | | | 348/70 |
| 2020/0196833 A1* | 6/2020 | Takahashi | A61B 1/00006 |

* cited by examiner

LIGHT INTENSITY

WHITE LIGHT

PUMPING LIGHT

WAVELENGTH

LIGHT INTENSITY (STANDARDIZATION)

L1

L2

700    800    900

WAVELENGTH (nm)

H1

H2

BRIGHTNESS
OF IMAGE

L16

L15

L14 dmin    d11                    dmax

SQUARE OF OBSERVATION DISTANCE

LIGHT
INTENSITY

L22    L21

I21

I22 d21

SQUARE OF OBSERVATION DISTANCE

GAIN OF
FLUORESCENCE
IMAGE

L44 d41

SQUARE OF OBSERVATION DISTANCE

GAIN OF
FLUORESCENCE
IMAGE

L51

SQUARE OF OBSERVATION DISTANCE

LUMINANCE VALUE

V→B     V→G

G→R

WAVELENGTH

LUMINANCE VALUE

L71

L72

WAVELENGTH

CONTROL DEVICE

CROSS-REFERENCE TO RELATED APPLICATION

This application is based on and claims priority under 35 U.S.C. § 119 to U.S. Provisional Application No. 63/522,779, filed Jun. 23, 2023, the entire contents of which are incorporated herein by reference.

BACKGROUND

1. Technical Field

The present disclosure relates to a control device.

2. Related Art

In an endoscope system, a technology is used in which a subject is irradiated with a narrow-band light so as to achieve enhancement in the viewability of a region of interest. At the time of performing fluorescent observation in which a pumping light is used as the narrow-band light, the region of interest gets illuminated due to the fluorescent material, thereby enabling achieving enhancement in the viewability of the region of interest. At the time of performing NBI observation (NBI stands for Narrow Band Imaging) in which the V (Violet) light or the G (Green) light is used as the narrow-band light, as a result of irradiating with an NBI light (the violet light or the green light) that is easily absorbable in the blood, it becomes possible to enhance the viewability of the blood vessels representing the region of interest.

In Japanese Patent Application Laid-open No. 2012-10962 is disclosed a technology in which: a white light image is generated based on an image signal captured as a result of irradiating a subject with a white light; a fluorescence image is generated based on an image signal captured as a result of irradiating the subject with a pumping light; and the white light image and the fluorescence image are synthesized to generate a synthetic image. Moreover, in Japanese Patent Application Laid-open No. 2012-10962, it is also disclosed that, if the light intensity of the pumping light and the light intensity of the white light is varied while maintaining a predetermined correlation therebetween, then the exposure balance between the white light image and an autofluorescence image can be maintained in an appropriate state.

SUMMARY

In some embodiments, one or more processors comprising hardware, the one or more processors being configured to: generate a white light image based on a first image signal captured as a result of irradiating a subject with a white light; generate a narrow-band light image based on a second image signal captured as a result of irradiating the subject with a narrow-band light; control a light intensity of the white light to a first value which is determined according to brightness of the white light image and according to a first ratio; and control a light intensity of the narrow-band light to a second value which is determined according to brightness of the narrow-band light image and according to a second ratio that is different than the first ratio.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
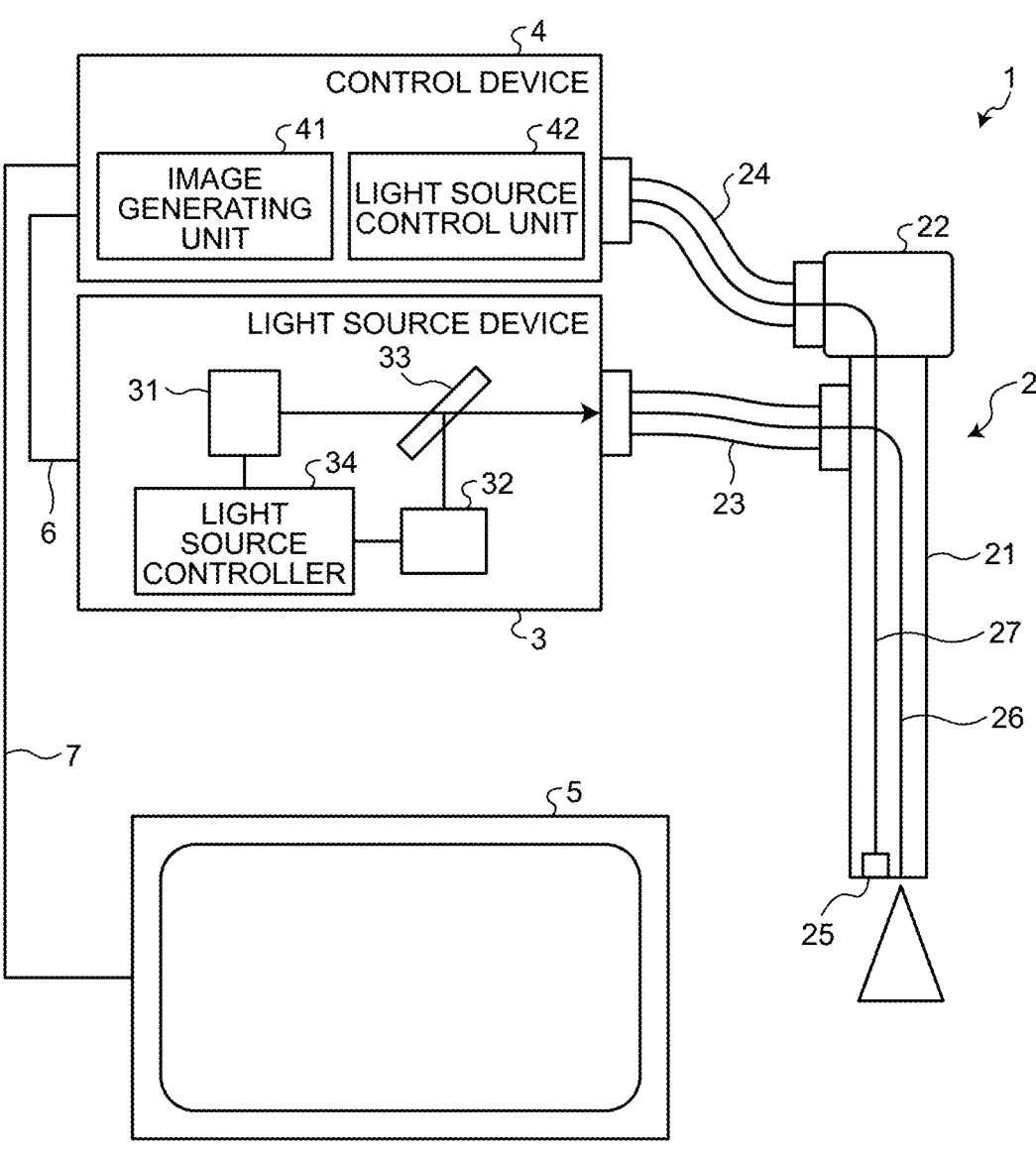
FIG. 1 is a diagram illustrating an overall configuration of an endoscope system according to embodiments.

Exemplary embodiments of a control device according to the disclosure are described below with reference to the accompanying drawings. However, the disclosure is not limited by the embodiments described below. The disclosure can be applied in general to a control device of an endoscope system that enables performing observation using a narrow-band light.

As far as the drawings are concerned, identical or corresponding elements are referred to by the same reference numerals. Moreover, each drawing is schematic in nature, and it may need to be kept in mind that the relationships among the dimensions of the elements or the ratio of the elements may be different than the actual situation. Among the drawings too, there may be portions having different relationships among the dimensions or having different ratios among the dimensions.

EMBODIMENTS

Configuration of Endoscope System

FIG. 1 is a diagram illustrating an overall configuration of an endoscope system according to the embodiments. An endoscope system 1 includes: an endoscope 2 that, when the front end portion thereof is inserted inside the subject, takes in-vivo images of the subject; a light source device 3 that generates an illumination light to be emitted from the front end of the endoscope 2; a control device 4 that performs predetermined signal processing with respect to imaging signals that are obtained by the endoscope 2 by performing imaging, and that comprehensively controls the overall operations of the endoscope system 1; a display device 5 that displays in-vivo images generated as a result of the signal processing performed by the control device 4; a connection cable 6 that connects the light source device 3 to the control device 4; and a signal cable 7 that connects the control device 4 to the display device 5.

The endoscope 2 includes: a flexible and elongated insertion portion 21; a grip 22 that is connected to the proximal end of the insertion portion 21; a light source connector 23 that extends from the grip 22 in a different direction than the direction of extension of the insertion portion 21 and that is connected to the light source device 3; a processor connector 24 that extends from the grip 22 in a different direction than the direction of extension of the insertion portion 21 and that is connected to the control device 4; an imaging element 25 that is disposed at the front end of the insertion portion 21; a light guide 26 that guides the light, which is emitted from the light source device 3, up to the front end of the insertion portion 21; and an image signal cable 27 that transmits image signals, which are generated by the imaging element 25, to the control device 4.

The imaging element 25 performs photoelectric conversion of the light coming from the subject, and generates image signals. The imaging element 25 is implemented using, for example, a CCD (Charge Coupled Device) image sensor or a CMOS (Complementary Metal Oxide Semiconductor) image sensor.

The light source device 3 includes: a white light source 31 that emits a white light (normal light) as the illumination light; a pumping light source 32 that emits a pumping light (narrow-band light) which causes excitation of a fluorescent material; a multiplexer 33 that multiplexes the white light emitted from the white light source 31 and the pumping light emitted from the pumping light source 32; and a light source controller 34 that, under the control performed by the control device 4, controls the light intensity and the light emission timing of the light emitted from the white light source 31 and the light emitted from the pumping light source 32.

As far as the white light source 31 is concerned, it is possible to use any one of various types of light sources such as an arc lamp, an LED, or a laser that can be used as a light source in an endoscope. Thus, the white light source 31 can be a white LED that emits only a white light, or can be a multicolor light source configured by combining a plurality of LEDs or lasers, such as by combining an R-LED, a G-LED, and a B-LED.

As far as the pumping light source 32 is concerned, it is possible to use any one of various types of light sources such as an arc lamp, an LED, or a laser that can be used as a light source in an endoscope. Thus, the pumping light source 32 either can be configured using a broad-spectrum light source and a band-pass filter, or can be an LED or a laser that emits light in a predetermined wavelength region. Still alternatively, the pumping light source 32 can be configured using a combination of an LED and a filter. The wavelength of the pumping light is selected according to the physical properties of the target material for observation. In the case of ICG (Indocyanine Green), it may be desirable that the wavelength of the pumping light is in the infrared region of around 800 nm. In the case of autofluorescence observation, it may be desirable that the wavelength of the pumping light is in the violet region or the blue region.

The control device 4 is configured either using a general-purpose processor such as a CPU (Central Processing Unit) or using a dedicated processor such as one of various arithmetic circuits, such as an ASIC (Application Specific Integrated Circuit), that implements specific functions; and also using a ROM (Read Only Memory) in which various programs are installed, and a RAM or a hard disk used to store the operation parameters and the data of various operations. The control device 4 includes an image generating unit 41 and a light source control unit 42.

The image generating unit 41 generates white light images (normal light images) and fluorescence images (narrow-band light images). Moreover, the image generating unit 41 generates superimposed images by superimposing white light images and fluorescence images. The image generating unit 41 generates image data based on the image signals obtained by the imaging element 25 by performing imaging. When the analog image signals are received from the endoscope 2, the image generating unit 41 performs A/D conversion and generates digital image data. Then, the image generating unit 41 performs a variety of image processing with respect to the received image signals and generates various images to be displayed in the display device 5.

The light source control unit 42 outputs a control signal meant for enabling the light source controller 34 to control the light intensity and the light emission timing of the light emitted from the white light source 31 and the light emitted from the pumping light source 32. Herein, the light source control unit 42 ensures that the normal light and the pumping light are emitted with a time difference between their emission. That enables obtaining the white light images and the fluorescence images in an independent manner.

The display device 5 is used to display the display images corresponding to the image data received from the control device 4 via the signal cable 7. The display device 5 is configured using a monitor made of liquid crystals or organic EL (Electro Luminescence).

First Embodiment

White Light and Pumping Light

Figure 2:
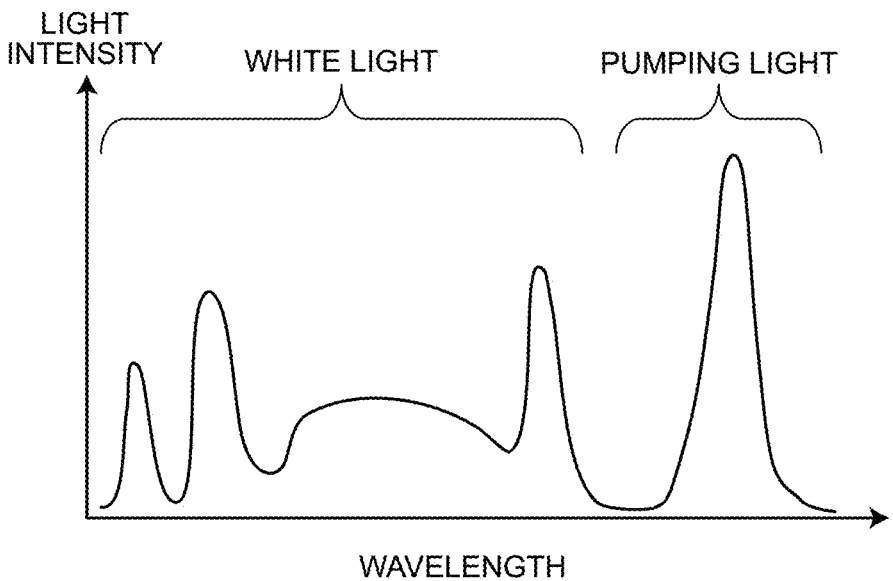
FIG. 2 is a diagram illustrating an example of the wavelength spectrum of the white light and the pumping light.

FIG. 2 is a diagram illustrating an example of the wavelength spectrum of the white light and the pumping light. In FIG. 2, the horizontal axis represents the wavelength, and the vertical axis represents the light intensity. Moreover, the short-wavelength side represents the spectrum of the white light, and the long-wavelength side represents the spectrum of the pumping light. The white light source 31 is configured, for example, by combining the following: an R (Red)-LED having the peak at 630 nm; a fluorescent-body pumping-type G (Green)-LED formed by combining a fluorescent body having the peak at 550 nm and a B (Blue)-LED; a B-LED having the peak at 460 nm; and a V (Violet)-LED having the peak at 415 nm. The pumping light source 32 causes excitation of the ICG representing the fluorescent material. Hence, an IR-LED having the peak at 780 nm is used in the pumping light source 32.

Figure 3:
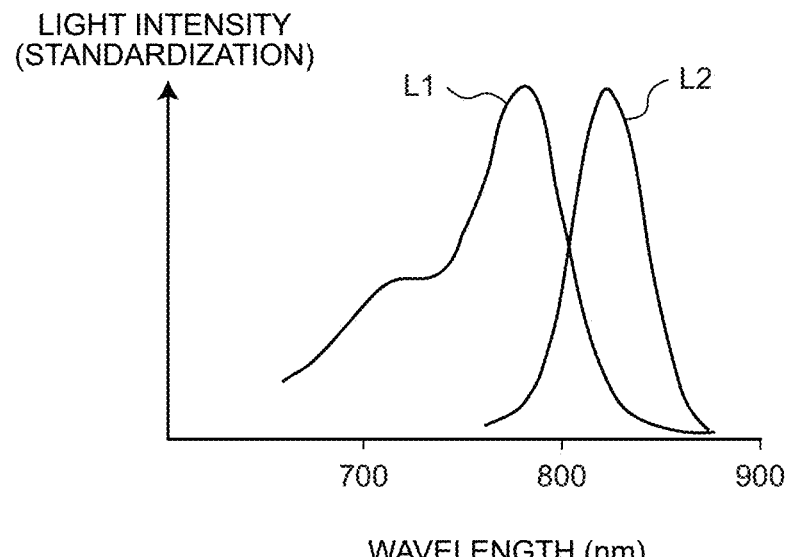
FIG. 3 is a diagram illustrating an example of the wavelength spectrum of the pumping light and the fluorescence.

FIG. 3 is a diagram illustrating an example of the wavelength spectrum of the pumping light and the fluorescence. In FIG. 3, the horizontal axis represents the wavelength, and the vertical axis represents the light intensity. Moreover, a line L1 representing the pumping light spectrum and a line L2 representing the fluorescence spectrum are standardized to have their peak values matched to each other. Herein, the ICG representing the fluorescent material absorbs the pumping light having the wavelength in the vicinity of 800 nm, and emits the IR light having the wavelength in the vicinity of 800 nm to 850 nm as fluorescence.

Imaging Element

In the case of generating a fluorescence image using the ICG, the imaging element 25 is configured to be capable of detecting the light in the IR region.

The imaging element 25 includes pixels capable of independently detecting, for example, the RGB light and the IR (Infrared) light. In that case, the V light and the B light are detected by the B pixels, the G light is detected by the G pixels, the R light is detected by the R pixels, and the fluorescence in the IR band is detected by the IR pixels. The fluorescence indicates the light having a longer wavelength than the wavelength of the pumping light and having a lower light intensity than the light intensity of the pumping light. For that reason, to the IR pixels, a filter is attached that cuts the wavelength region of the pumping light and enables passage of the fluorescence present on the long-wavelength side of that wavelength region. The filter either can be attached only to the IR pixels or can be attached to the entire imaging element 25. In the case of attaching a filter to the entire imaging element 25, such a filter is used which enables passage of the RGB light and the fluorescence and which cuts only the pumping light.

Meanwhile, the imaging element 25 can be configured to include RGB pixels among which the R pixels have a sensitivity toward the IR region. In that case, to the R pixels, a filter is attached that enables passage of the R light and the fluorescence in the IR band and that cuts the pumping light. The filter either can be attached only to the IR pixels or can be attached to the entire imaging element 25. In the case of attaching a filter to the entire imaging element 25, such a filter is used which enables passage of the RGB light and the fluorescence and which cuts only the pumping light.

Operations of Control Device

Figure 4:
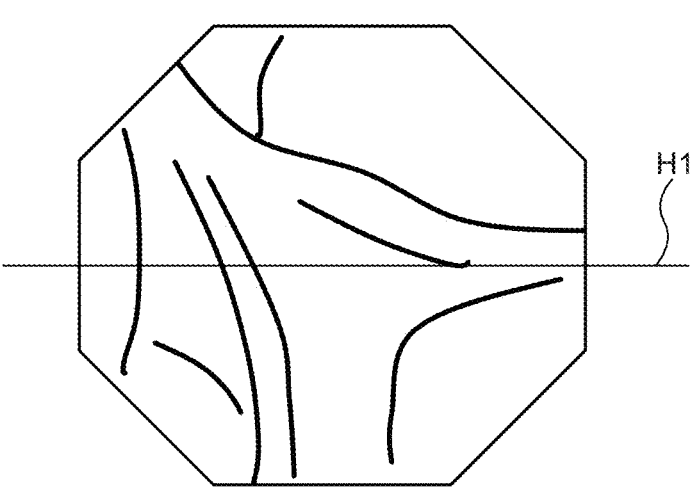
FIG. 4 is a diagram illustrating an example of a white light image.

The image generating unit 41 generates a white light image based on an image signal captured as a result of irradiating the subject with a white light. FIG. 4 is a diagram illustrating an example of a white light image. The white light image enables visual confirmation of the structure of the body tissue.

Figure 5:
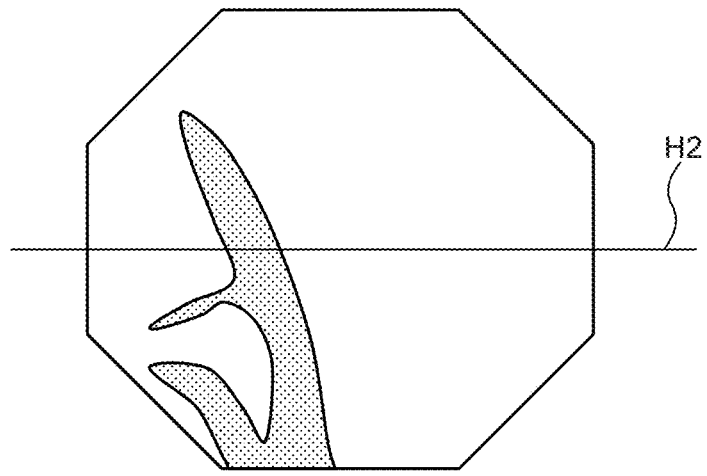
FIG. 5 is a diagram illustrating an example of a fluorescence image.

The image generating unit 41 generates a fluorescence image based on an image signal captured as a result of irradiating the subject with a pumping light. FIG. 5 is a diagram illustrating an example of a fluorescence image. A fluorescence image represents an image of the fluorescence that has been excited by the pumping light, and that region in the image in which the ICG representing a fluorescent material is present (in FIG. 5, the hatched region) appears bright.

Figure 6:
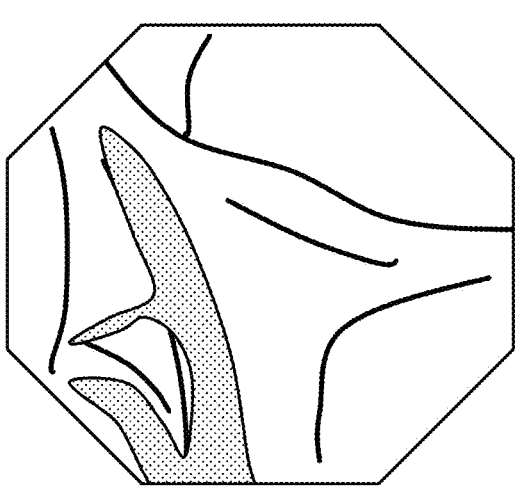
FIG. 6 is a diagram illustrating an example of a superimposed image.

The image generating unit 41 generates a superimposed image by superimposing the white light image and the fluorescence image. FIG. 6 is a diagram illustrating an example of a superimposed image. In a superimposed image, the region in which the ICG is present is displayed to be bright based on the fluorescence image, and the surrounding tissue is displayed based on the white light image. Hence, in the body tissue of the subject, it becomes easier to figure out the region in which the ICG is present. For example, in the case of performing a surgery to remove only the region in which the ICG is present, the superimposed image makes it possible to easily figure out the region to be removed.

In a superimposed image, the brightness of the white light image is set to be equivalent to or a little lower than the brightness in the case in which an image based only on the white light is displayed in the display device 5 (i.e., in the case of normal observation). In a superimposed image, the white light image represents the background image. That is because, as long as the positional relationship of the organs and the treatment tools can be figured out, there is no need to demonstrate the details.

On the other hand, in a superimposed image, it may be desirable to have such a brightness of the fluorescence image that there is an increase in the contrast between the region in which the ICG representing the region of interest is present and the region in which the ICG is not present. A fluorescence image is meant for confirming the region in which the ICG is present. Hence, it may be desirable to have such a fluorescence image in which there is a conspicuous difference between the region in which the ICG is present and the region in which the ICG is not present. In other words, as long as a high contrast is achieved for the region of interest, it is fine even if the overall fluorescence image is too bright.

Figure 7:
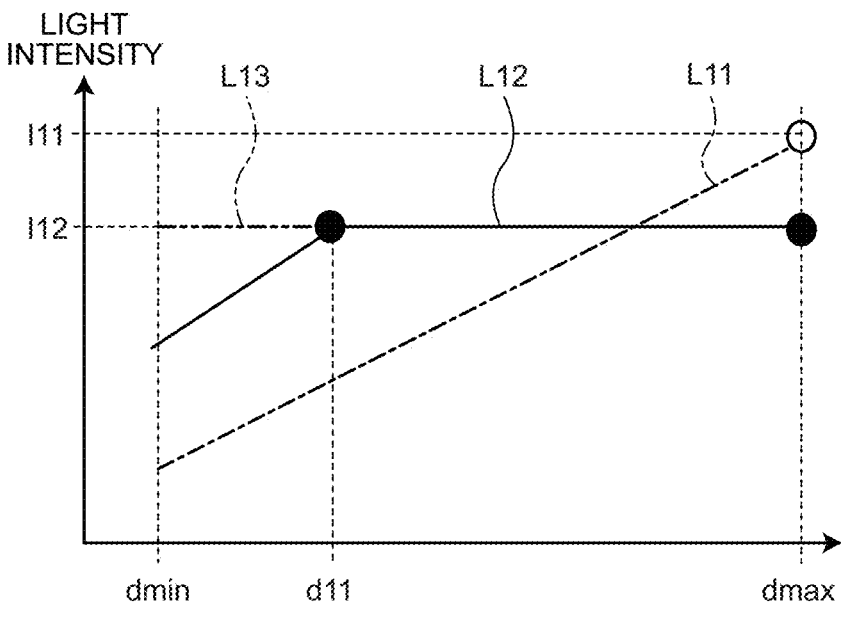
FIG. 7 is a diagram illustrating the light intensity of the white light and the light intensity of the pumping light.

FIG. 7 is a diagram illustrating the light intensity of the white light and the light intensity of the pumping light. In FIG. 7, the horizontal axis represents the square of the observation distance (i.e., the distance between the subject and the front end of the insertion portion 21), and the vertical axis represents the light intensity. Moreover, a line L11 represents the light intensity of the white light, and a line L12 represents the light intensity of the pumping light.

Figure 8:
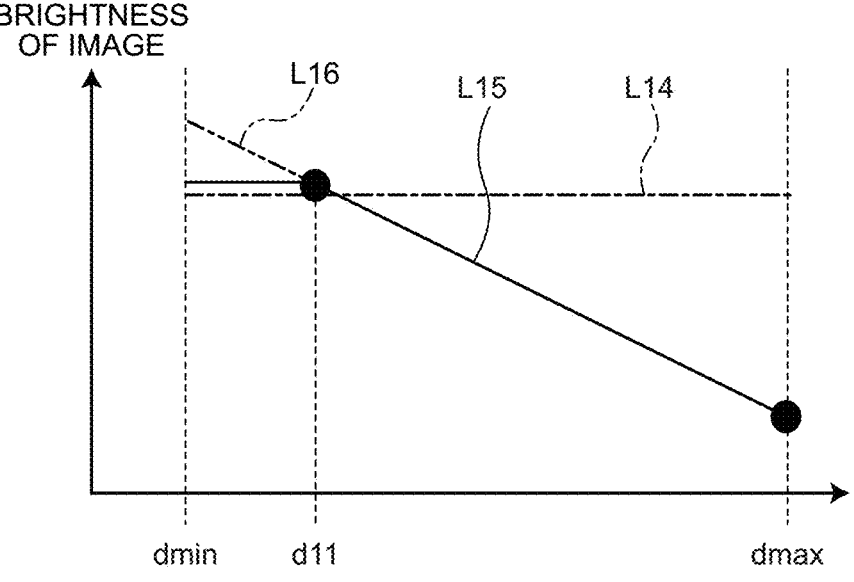
FIG. 8 is a diagram illustrating the brightness of a white light image and the brightness of a fluorescence image.

FIG. 8 is a diagram illustrating the brightness of a white light image and the brightness of a fluorescence image. In FIG. 8, the horizontal axis represents the square of the observation distance in an identical manner to FIG. 7, and the vertical axis represents the image brightness. Moreover, a line L14 represents the brightness of the white light image, and a line L15 represents the brightness of the fluorescence image.

As illustrated in the line L14, the light source control unit 42 controls the light intensity of the white light in such a way that the brightness of the white light image remains constant regardless of the observation distance. Herein, regarding the light that is irradiated onto the subject from the front end of the insertion portion 21 and that falls on the imaging element 25 after reflecting from the subject, the light intensity decreases in proportion to the square of the observation distance. In that regard, as illustrated in the line L11, the light source control unit 42 can control the light intensity of the white light to a value that is decided according to the brightness of the white light image and according to a first ratio, and can ensure that the brightness of the white light image remains constant regardless of the observation distance.

Moreover, as illustrated in the line L15, from a minimum distance dmin to a distance d11, the light source control unit 42 controls the light intensity of the pumping light in such a way that the brightness of the fluorescence image remains constant regardless of the observation distance. In an identical manner to the white light, as illustrated in the line L12, the light source control unit 42 can control the light intensity of the pumping light to a value that is decided according to the brightness of the fluorescence image and according to a second ratio which is different than the first ratio, and can ensure that the brightness of the fluorescence image remains constant regardless of the observation distance. The first ratio and the second ratio are mutually different values, and there is no correlation between the light intensity of the white light and the light intensity of the pumping light.

Moreover, as illustrated in the line L12, from the distance d11 to a maximum distance dmax, the light source control unit 42 controls the light intensity of the pumping light to a predetermined light intensity. Herein, the predetermined light intensity represents, for example, the upper limit light intensity that is preset in order to avoid the generation of heat at the front end of the insertion portion 21 or to avoid an increase in the temperature of the biological object due to light absorption. When the brightness of the fluorescence image is equal to or higher than a threshold value, the light source control unit 42 controls the light intensity of the pumping light to a predetermined light intensity, so that the light intensity of the pumping light can be prevented from exceeding the upper limit light intensity.

Moreover, at the minimum distance dmin too, if the brightness of the fluorescence image is lower than a threshold value; then, as illustrated in the line L13, the light intensity of the pumping light can be set to the upper limit threshold value up to the minimum distance dmin. At that time, as illustrated in the line L16, shorter the observation distance till the minimum distance dmin, the higher becomes the brightness of the fluorescence image.

According to the first embodiment described above, the light intensity of the pumping light can be set to a high value without any correlation to the light intensity of the white light. That enables achieving enhancement in the viewability of the fluorescence image. Meanwhile, if the observation distance is shorter than the distance d11, then the brightness of the fluorescence image can be kept constant regardless of the observation distance. On the other hand, when the observation distance is equal to or longer than the distance d11, the light intensity of the pumping light can be set to the upper limit light intensity.

Moreover, in the first embodiment, the explanation is given about the case in which, at the time of controlling the light intensity of the pumping light to a predetermined light intensity, the predetermined light intensity is set to a preset value. For example, based on various safety standards, the preset value can be set to such a light intensity that, when the front end of the insertion portion 21 makes contact with a biological object, the pumping light does not exert a negative effect on the biological object. Moreover, for example, based on various safety standards, the preset value can be set to such a light intensity that there is no heat generated in the insertion portion 21 due to the pumping light and that there is no negative effect on the biological object.

Alternatively, the predetermined light intensity can be set according to the parameters related to fluorescence images. When the observation distance is the shortest, the light intensity can be set in such a way that the luminance value of the fluorescence images does not exceed the maximum value.

Still alternatively, the predetermined light intensity can be set according to the parameters related to the devices constituting the imaging element 25 that performs imaging of the subject. The light intensity can be set according to the transmittance of the pumping light in the filter that is included in the imaging element 25 for cutting the pumping light. In a fluorescence image, the light intensity of the pumping light may be required to be sufficiently lower than (for example, $\frac{1}{20}$-th of) the light intensity of the white light. Hence, the upper limit light intensity of the pumping light can be set to satisfy that condition. Alternatively, the light intensity can be set according to the lowest shutter speed of the electronic shutter included in the imaging element 25. When the shutter speed is at the lowest, the upper limit light intensity of the pumping light can be set in such a way that the luminance value of the fluorescence image does not exceed the maximum value.

Still alternatively, the predetermined light intensity can be set according to the observation mode. Assume that it is possible to switch between a fluorescent region identification mode meant for identification of the fluorescent region and a normal superimposition mode meant for normal fluorescent observation. In that case, in the fluorescence region identification mode, the upper limit light intensity of the pumping light can be set to a high value; and, in the normal superimposition mode, the upper limit light intensity of the pumping light can be set to a low value.

Still alternatively, the predetermined light intensity can be set according to the observation distance. When the main observation distance can be estimated in advance according to the usage, the upper limit light intensity of the pumping light can be set to enable achieving enhancement in the viewability at the main observation distance.

Modification Example 1-1

In the first embodiment, the upper limit of the brightness of the fluorescence images can be set in an arbitrary manner according to the user input. When the observation distance is short, the fluorescence images become bright. Thus, as the upper limit of the brightness of the fluorescence images, the user can set such a brightness at which the fluorescence image feels too bright and the viewability feels to be poor.

Figure 9:
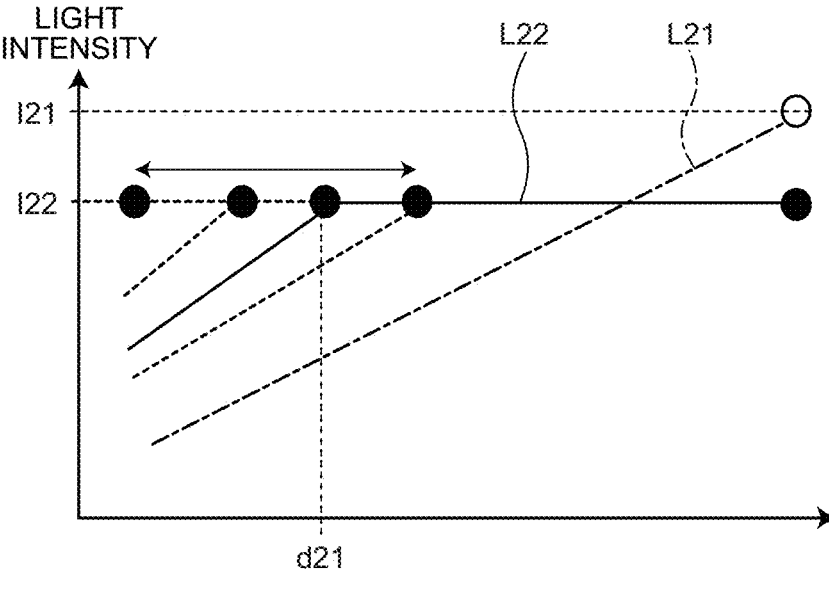
FIG. 9 is a diagram illustrating the light intensity of the white light and the light intensity of the pumping light.

FIG. 9 is a diagram illustrating the light intensity of the white light and the light intensity of the pumping light. A fluorescence image becomes bright when the observation distance is short. Thus, when the observation distance is shorter than a distance d21, the light intensity of the pumping light is reduced. That is, the distance d21 changes according to the upper limit of the brightness of the fluorescence images as set by the user.

Alternatively, the upper limit of the brightness of the fluorescence images can be set to such a level that the maximum contrast is achieved between the region in which the ICG, which represents the region of interest, is present and the region in which the ICG is not present.

Figures 10, 11:
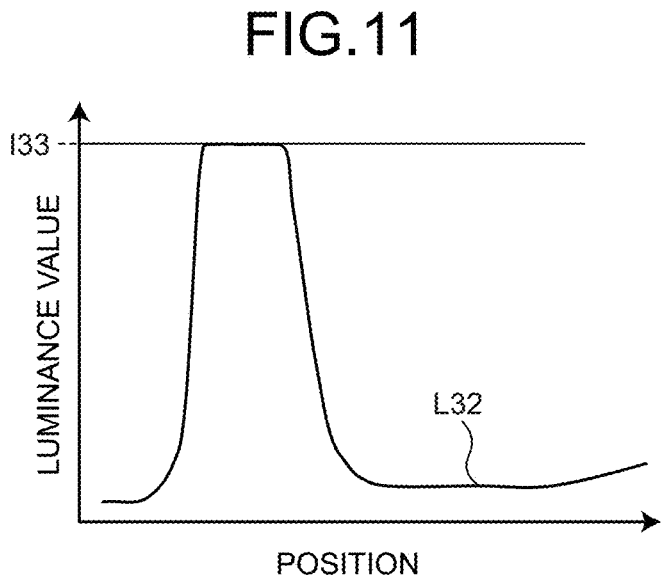
FIG. 10 is a diagram illustrating the luminance values of white light images.
FIG. 11 is a diagram illustrating the luminance values of fluorescence images.

FIG. 10 is a diagram illustrating the luminance values of white light images. The luminance values illustrated in FIG. 10 correspond to the luminance values on a horizontal line H1 illustrated in FIG. 4. As illustrated in FIG. 10, a luminance value I32 representing the upper limit luminance value of the white light images is set to be sufficiently smaller than a luminance value I31 at which overexposure occurs. Hence, as illustrated in a line L31, the white light images are controlled to have a lower luminance value than the luminance value I32.

FIG. 11 is a diagram illustrating the luminance values of fluorescence images. The luminance values illustrated in FIG. 5 correspond to the luminance values on a horizontal line H2 illustrated in FIG. 5. As illustrated in a line L32 illustrated in FIG. 11, although the region having high luminance values reaches a luminance value I33 at which overexposure occurs, there is a high contrast between the region of interest (i.e., the region in which overexposure occurs) and the remaining region. In this way, the upper limit of the brightness of the fluorescence images can be set to achieve the maximum contrast for the region of interest.

Meanwhile, in addition to taking into account the contrast, the upper limit of the brightness of the fluorescence images can be set according to the peak and the bottom of the luminance values of the fluorescence images. Still alternatively, the upper limit of the brightness of the fluorescence images can be set to enable achieving enhancement in the viewability using AI.

Modification Example 1-2

In the first embodiment, the upper limit of the brightness of the fluorescence images can be set according to the proportion of the region in which overexposure is occurring in the fluorescence images.

Figure 12:
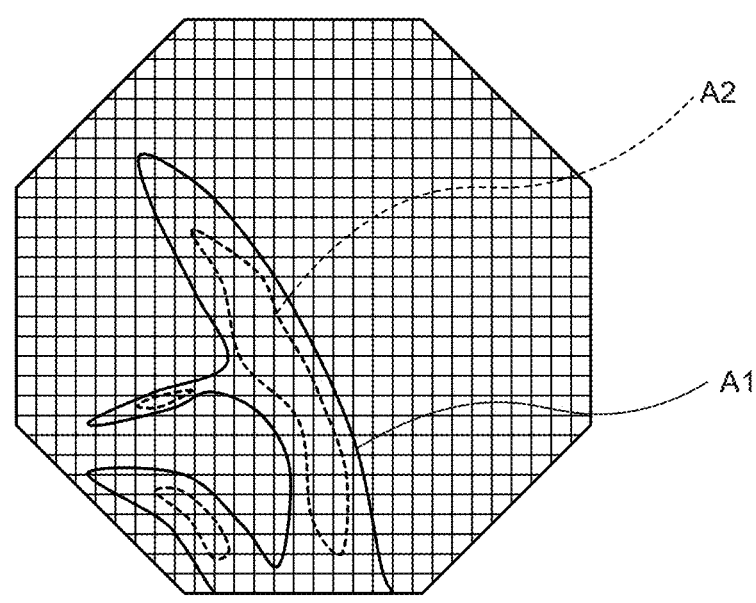
FIG. 12 is a diagram illustrating a fluorescence image.

FIG. 12 is a diagram illustrating a fluorescence image. In FIG. 12 are illustrated pixels included in the fluorescence image or pixel blocks made of a plurality of pixels. A region A1 represents a region in which the luminance values of the pixels indicate the fluorescence to be equal to or greater than a threshold value. A region A2 represents a region in which overexposure has occurred. The upper limit of the brightness of the fluorescence images is set in such a way that the value obtained by dividing the pixel count in the region A2 by the total pixel count in a fluorescence image is equal to or smaller than a threshold value. As a result, the upper limit of the brightness of the fluorescence images can be automatically set to an appropriate brightness.

Regarding the proportion of the region in which overexposure has occurred, although there is no restriction, it may be desirable to have the proportion to be equal to, for example, about 10%. Moreover, if a photographic subject such as treatment tool or a forceps that can easily cause overexposure has been captured, then the region in which overexposure has occurred can be set by excluding the pixels corresponding the overexposure occurring due to that photographic subject. Moreover, if a photographic subject that can easily cause overexposure has been captured, then the impact of that photographic subject can be adjusted by multiplying a balance coefficient equal to or smaller than "1" to the photographic subject.

Meanwhile, if the overexposure region has reached the boundary of the region of interest, then the overexposure region in the vicinity of that boundary can be excluded from the region considered to have overexposure. As far as the region to be excluded is concerned, the region in which the overexposure has occurred in cluster can be removed in entirety. Alternatively, the impact of the overexposure region, in which the overexposure has occurred in cluster, can be adjusted by multiplying a balance coefficient equal to or smaller than "1" to the overexposure region.

Second Embodiment

In a second embodiment, the light intensity of the white light and the light intensity of the pumping light can be identical to the light intensity illustrated in FIG. 7. Herein, in order to ensure that the brightness of a white light image is equal to a predetermined value, the image generating unit 41 performs gain correction with respect to the white light image and generates an image. Moreover, in order to ensure that the brightness of a fluorescence image is equal to a predetermined value, the image generating unit 41 performs gain correction with respect to the fluorescence image and generates an image.

Figure 13:
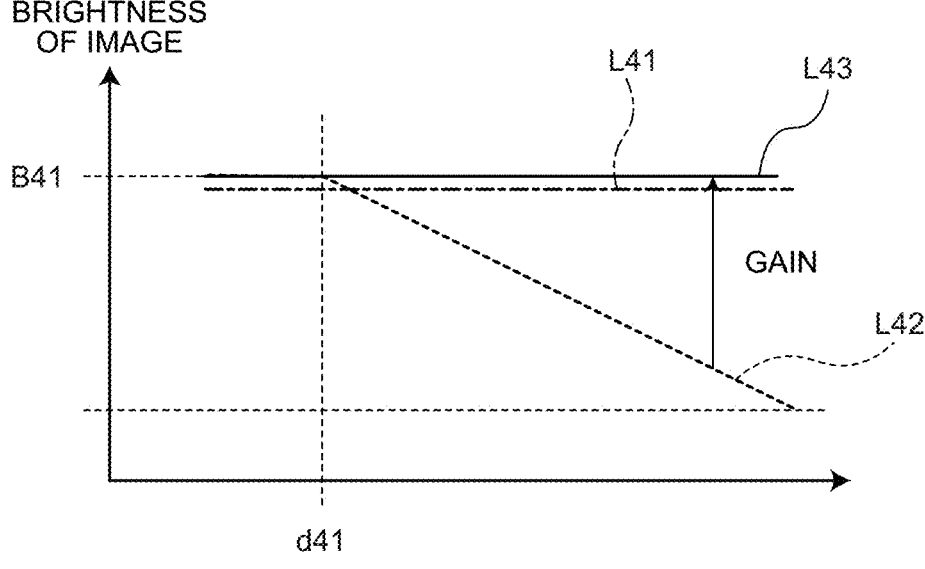
FIG. 13 is a diagram illustrating the brightness of a white light image and the brightness of a fluorescence image.

FIG. 13 is a diagram illustrating the brightness of a white light image and the brightness of a fluorescence image. A line L41 represents the brightness of the white light image, a line L42 represents the brightness of the fluorescence image that is not subjected to gain correction, and a line L43 represents the brightness of the fluorescence image that has been subjected to gain correction.

As illustrated in the line L43, the image generating unit 41 performs gain correction in such a way that the brightness of the fluorescence image becomes substantially constant regardless of the observation distance. In the region having the observation distance equal to or greater than a distance d41, the image generating unit 41 sets the gain with respect to the fluorescence to a value that is decided according to the brightness of the fluorescence image and according to a third ratio. Moreover, in the region present at a shorter observation distance than the distance d41, the image generating unit 41 does not apply any gain because the brightness of the fluorescence image is equal to greater than a threshold value. As a result of performing gain correction in this way, the brightness of the fluorescence image becomes constant regardless of the observation distance, and the ratio of the white light image and the fluorescence image becomes constant in the superimposition image. That enables achieving reduction in the sense of discomfort felt by the user when the observation distance changes.

Meanwhile, the image generating unit 41 sets the gain with respect to the white light image and the gain with respect to the fluorescence image in such a way that the ratio between the brightness of the white light image and the brightness of the fluorescence image becomes substantially constant. With that, the ratio between the brightness of the white light image and the brightness of the fluorescence image becomes substantially constant regardless of the observation distance, thereby enabling achieving reduction in the sense of discomfort felt by the user when the observation distance changes.

Figure 14:
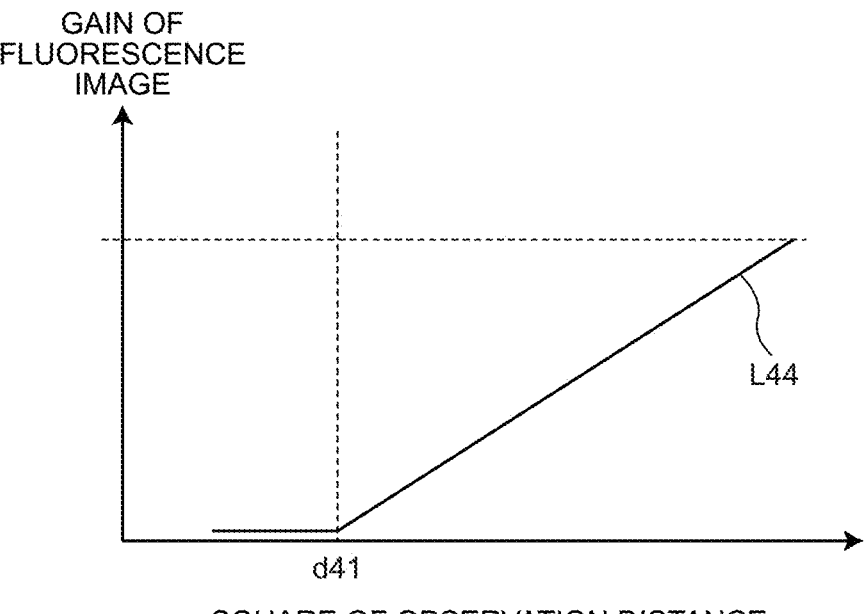
FIG. 14 is a diagram illustrating the gain of a fluorescence image.

FIG. 14 is a diagram illustrating the gain of the fluorescence image. In FIG. 14, as illustrated in a line L44, as the observation distance increases with reference to the distance d41, there is an increase in the magnitude of the gain to be applied to the fluorescence image. Meanwhile, the noise of the fluorescence image increases in proportion to the magnitude of the gain. Hence, in the region present at a short observation distance, the gain can be lowered and the noise can be reduced.

Figure 15:
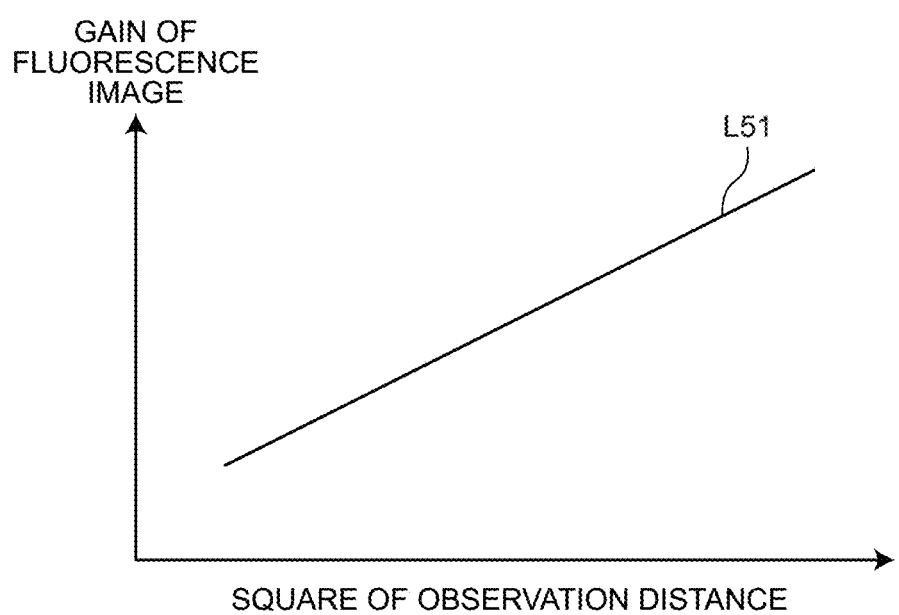
FIG. 15 is a diagram illustrating the gain of a fluorescence image.

FIG. 15 is a diagram illustrating the gain of the fluorescence image. As illustrated in a line L16 in FIG. 8, till the minimum distance dmin, the light intensity of the pumping light is treated as the upper limit light intensity. In that case, as illustrated in a line L51 in FIG. 15, shorter the observation distance till the minimum distance dmin, the gain can be reduced accordingly. Thus, shorter the observation distance, the more is the achievable reduction in the gain, and hence the noise can be reduced.

Modification Example 2-1

As explained in the modification example 1-1 with reference to FIG. 9, in the case of arbitrarily setting the upper limit of the brightness of the fluorescence images according to the user input, gain correction can be performed according to that brightness.

Figure 16:
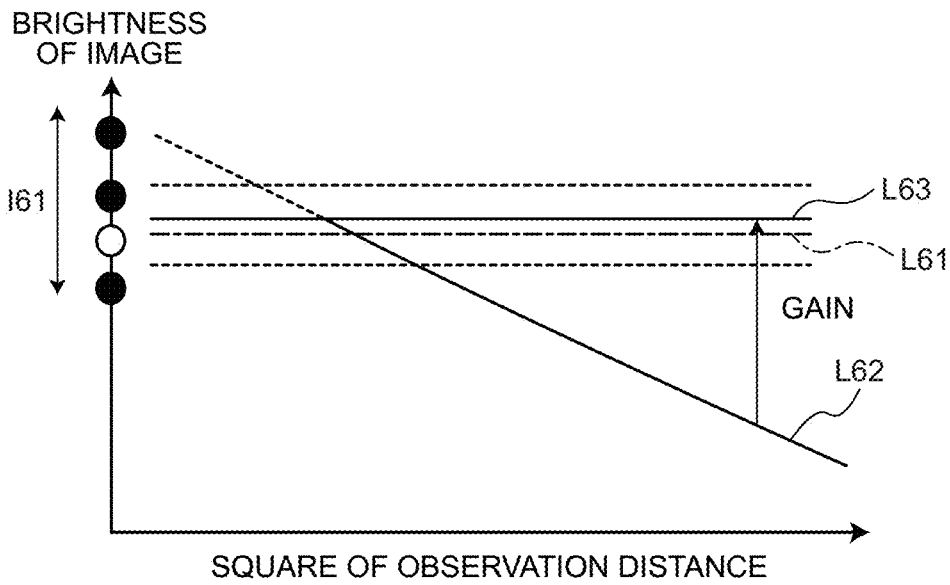
FIG. 16 is a diagram illustrating the brightness of a white light image and the brightness of a fluorescence image.

FIG. 16 is a diagram illustrating the brightness of a white light image and the brightness of a fluorescence image. A line L61 represents the brightness of the white light image, a line L62 represents the brightness of the fluorescence image that is not subjected to gain correction, and a line L63 represents the brightness of the fluorescence image that has been subjected to gain correction.

As illustrated in FIG. 16, a brightness 161 representing the upper limit of the brightness of the fluorescence images is arbitrarily set according to the user input. At that time, according to the brightness 161, gain correction is performed in such a way that the brightness of the fluorescence image remains constant regardless of the observation distance.

Figure 17:
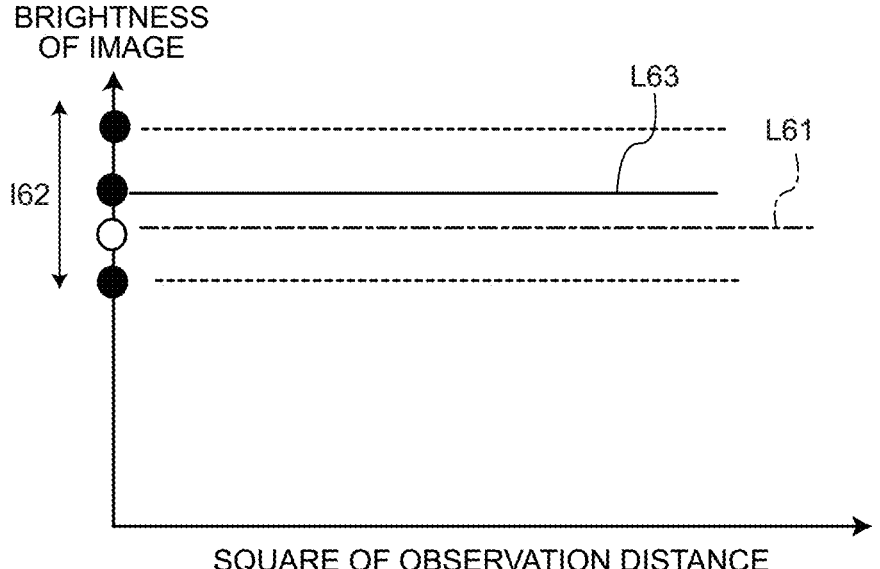
FIG. 17 is a diagram illustrating the brightness of a white light image and the brightness of a fluorescence image.

FIG. 17 is a diagram illustrating the brightness of a white light image and the brightness of a fluorescence image. As illustrated in FIG. 17, when a brightness 162 representing the upper limit of the brightness of the fluorescence image is arbitrarily set according to the user input, the gain can be varied in a stepwise manner according to the brightness 162. In that case, the image generating unit 41 can perform gain correction with respect to the fluorescence image and generate an image in such a way that the brightness of the fluorescence image becomes equal to or greater than a predetermined value. In an identical manner, the light intensity of the pumping light can also be varied in a stepwise manner according to the brightness I62.

Third Embodiment

White Light and NBI Light

Figure 18:
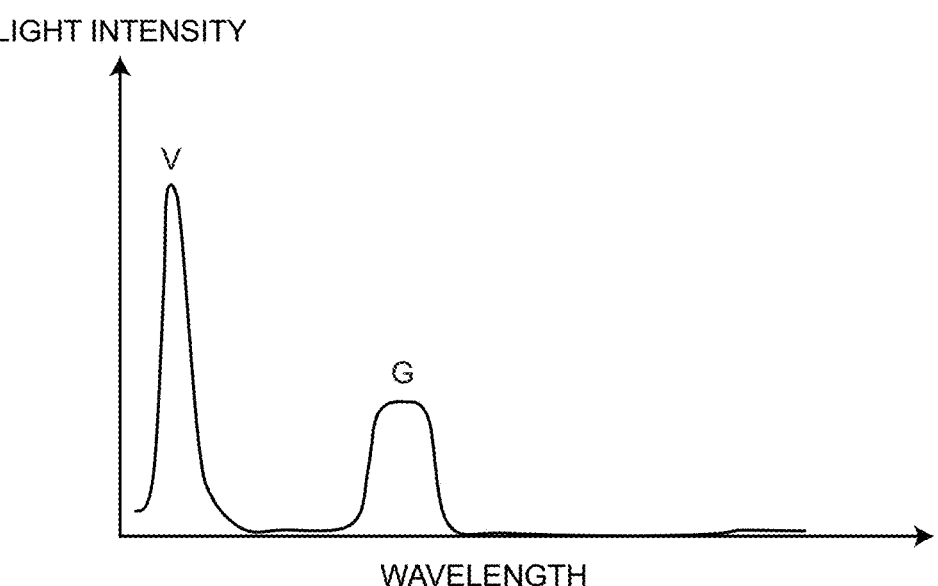
FIG. 18 is a diagram illustrating an example of the wavelength spectrum of the NBI light.

FIG. 18 is a diagram illustrating an example of the wavelength spectrum of the NBI light. As illustrated in FIG. 18, the NBI light includes the V light representing the violet narrow-band light and includes the G light representing the green narrow-band light. At the time of performing NBI observation, as a result of irradiating with the NBI light (the V light and the G light) that is easily absorbable in the hemoglobin included in the blood, it becomes possible to enhance the viewability of the blood vessels representing the region of interest.

Figure 19:
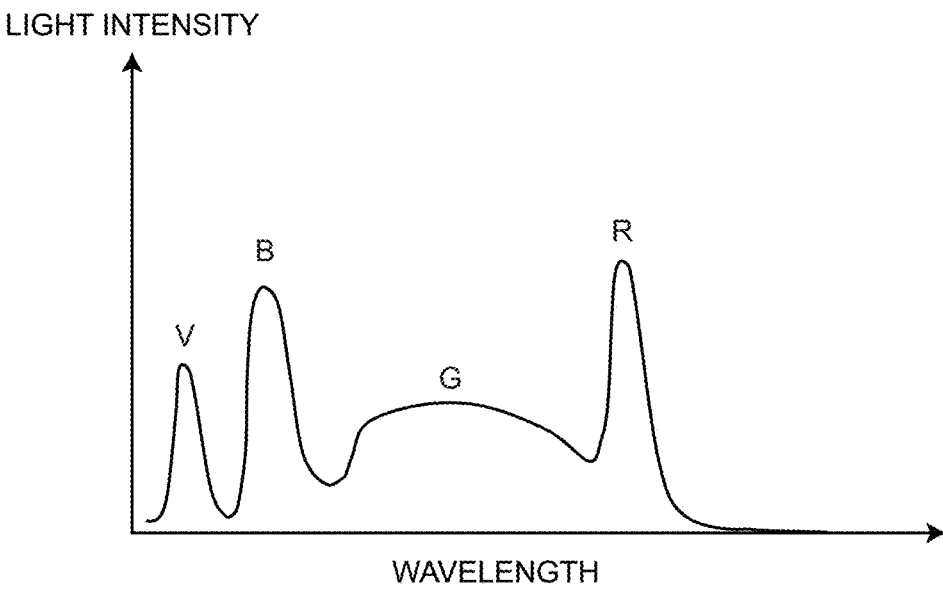
FIG. 19 is a diagram illustrating an example of the wavelength spectrum of the white light.

FIG. 19 is a diagram illustrating an example of the wavelength spectrum of the white light. The white light illustrated in FIG. 19 is identical to the white light illustrated in FIG. 2. Hence, that explanation is not given again.

In an NBI image taken by irradiating with the NBI light, a background of the NBI image has the same color as the color of the irradiated NBI light. Hence, when an NBI image is superimposed without modification onto a white light image, the background image happens to have a strong color shade of the NBI light. For that reason, a sufficiently high contrast cannot be obtained between the region of interest and the background color. In a third embodiment, the color balance of the white light image is adjusted so as to correct the color shade of the background image of the NBI image. That enables bringing the background color closer to the natural white color, thereby enabling achieving enhancement in the viewability of the blood vessels representing the region of interest.

Figures 20, 21:
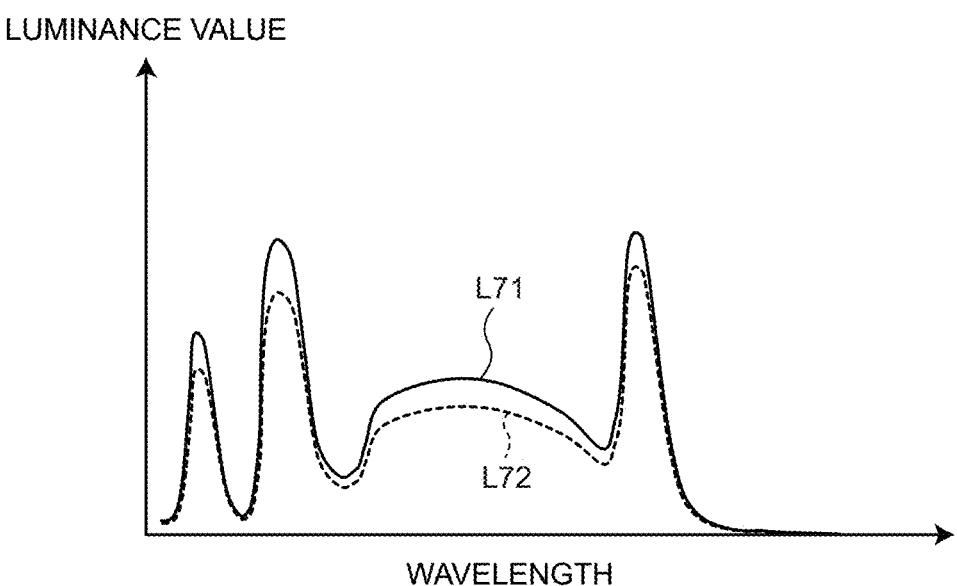
FIG. 20 is a diagram illustrating the conversion of the wavelength of the NBI light.
FIG. 21 is a diagram illustrating the color balance of a superimposed image and the color balance of a post-correction white light image.

FIG. 20 is a diagram illustrating the conversion of the wavelength of the NBI light. As illustrated in FIG. 20, an RGB image that is taken by irradiating with the NBI light is subjected to color conversion, and an NBI image for display is generated. An image taken by irradiating with the G light and capturing the reflected light is treated as the R image and an image taken by irradiating with the V light and capturing the reflected light is treated as the G image and the B image; and those images are subjected to color conversion and an NBI image for display is generated.

FIG. 21 is a diagram illustrating the color balance of the superimposed image and the color balance of the post-correction white light image. A line L71 represents the color balance of the superimposed image, and a line L72 represents the color balance of the post-correction white light image. In the superimposed image, the NBI image includes B, G, and R components. Hence, if the white light image is superimposed without modification, then the superimposed image happens to have a strong color shade of the B, G, and R components. In order to reduce that impact, the color balance of the white light image is corrected in such a way that the R light component of the white light image is reduced by an amount equivalent to the G light component of the NBI light and that the B light component and the G light component of the white light image are reduced by an amount equivalent to the V light component of the NBI light. Thus, when the white light illustrated in FIG. 19 is corrected to have the color balance illustrated by a line L72, the color shade becomes substantially same as the case of the application of the white light. Hence, it becomes possible to perform observation in a natural color shade, and to enhance the viewability of the blood vessels representing the region of interest.

Figure 22:
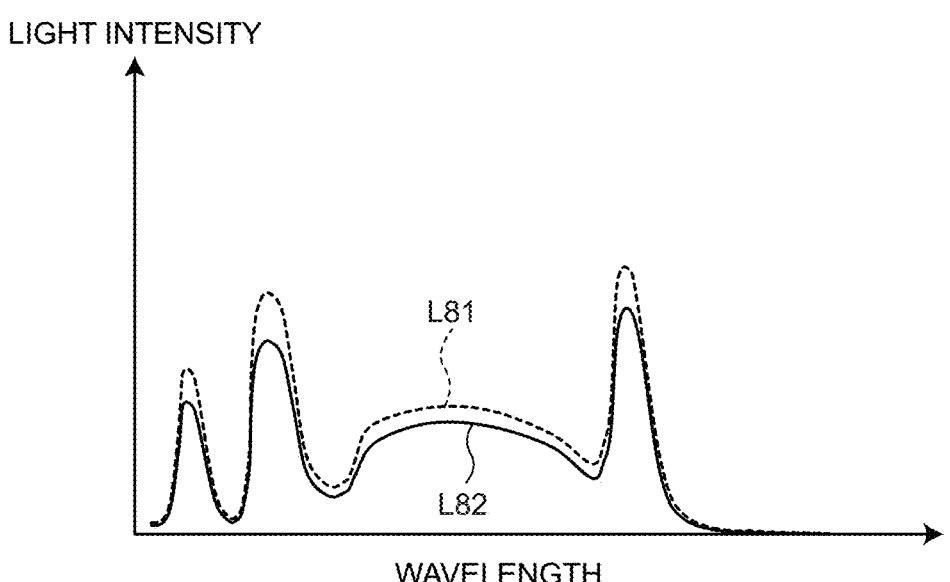
FIG. 22 is a diagram illustrating the wavelength spectrum of the post-correction white light.

FIG. 22 is a diagram illustrating the wavelength spectrum of the post-correction white light. A light L81 represents the wavelength spectrum of the pre-correction white light, and a line L82 represents the wavelength spectrum of the post-correction white light. In an identical manner to the correction of the color balance, the light intensity balance of the white light can be corrected in such a way that the R light component of the white light is reduced by an amount equivalent to the G light component and that the B light component and the G light component of the white light image are reduced by an amount equivalent to the V light component of the NBI light.

Figure 23:
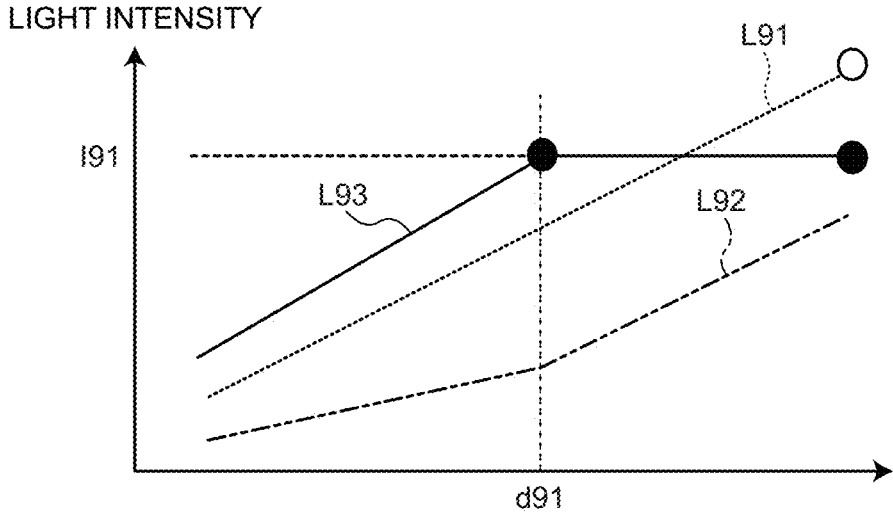
FIG. 23 is a diagram illustrating the light intensity of the white light and the light intensity of the pumping light.

FIG. 23 is a diagram illustrating the light intensity of the white light and the light intensity of the pumping light. A line L91 represents the light intensity of the pre-correction white light, a line L92 represents the light intensity of the post-correction white light, and a line L93 represents the light intensity of the NBI light.

As illustrated in the line L91, the light intensity of the pre-correction white light increases in proportion to the observation distance. On the other hand, as illustrated in the line L93, in the region present at a shorter observation distance than a distance d91, the light intensity of the NBI light decreases in proportion to the decrease in the observation distance; and, in the region present at a longer observation distance the distance d91, the light intensity of the NBI light is set to the upper limit light intensity. Then, the post-correction light intensity of the white light illustrated in the light L92 is reduced in association with the light intensity of the NBI light. Hence, in the region present at a shorter observation distance than the distance d91; shorter the observation distance, the smaller is the amount of reduction in the white light. On the other hand, in the region present at the observation distance equal to or longer than the distance d91, the light intensity of the NBI light becomes constant and thus the amount of reduction in the white light also becomes constant.

As explained above in the third embodiment, the light intensity of the NBI light can be set to a high value without any correlation to the light intensity of the white light. That enables achieving enhancement in the viewability of the NBI image. Moreover, regardless of the observation distance, the background color of the superimposed image has the substantially same color shade as the color shade in the case of the application of the white light. Hence, it becomes possible to perform observation in a natural color shade, and to enhance the viewability of the blood vessels representing the region of interest.

Meanwhile, in the third embodiment, the explanation is given about an example in which the light intensity balance of the white light is corrected according to the NBI light that includes the V light and the G light. However, that is not the only possible case. Alternatively, for example, using ALM-488 that is a fluorescent material used in revealing the nerves, when a blue pumping light having the wavelength in the vicinity of 480 nm is to be applied, a filter for cutting the pumping light is installed in the imaging element 25. In that case, the components of the pumping light that pass through the filter affect the color shade of the background. In that regard, the light intensity balance of the white light can be corrected by an amount equal to the transmitted light of the pumping light. In an identical manner, the color balance of the white light image can be corrected by an amount equal to the transmitted light of the pumping light.

Modification Example 3-1

In the third embodiment, the explanation is given about an example in which color conversion is performed with respect to an NBI image, and a superimposed image is generated. Alternatively, a superimposed image can be generated without performing color conversion with respect to an NBI image.

Figure 24:
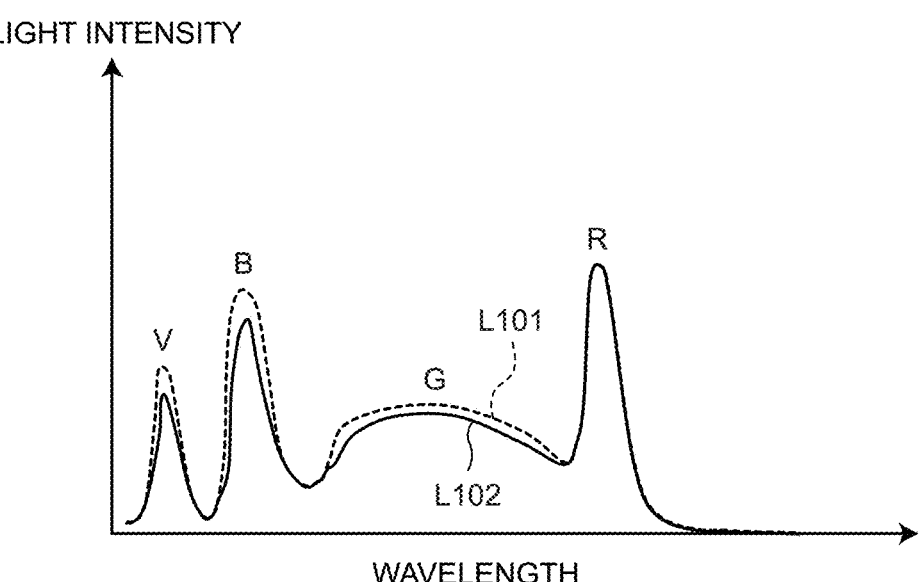
FIG. 24 is a diagram illustrating the wavelength spectrum of the post-correction white light.

FIG. 24 is a diagram illustrating the wavelength spectrum of the post-correction white light. A line L101 represents the wavelength spectrum of the pre-correction white light, and a line L102 represents the wavelength spectrum of the post-correction white light. As illustrated in FIG. 18, since the NBI light includes the V light component and the G light component, the V light component of the white light can be reduced by an amount equivalent to the V light component of the NBI light, and the G light component of the white light can be reduced by an amount equivalent to the G light component of the NBI light. As a result, the background color of the superimposed image has the substantially same color shade as the color shade in the case of the application of the white light. Hence, it becomes possible to perform observation in a natural color shade, and to enhance the viewability of the blood vessels representing the region of interest.

Fourth Embodiment

In the first embodiment, the explanation is given about controlling the light intensity of the white light and the light intensity of the pumping light without any correlation therebetween. Moreover, as explained in the third embodiment, the color balance of the white light image or the light intensity balance of the white light can be adjusted according to the fluorescence. As illustrated in FIG. 3, the wavelength of the fluorescence indicates the IR light having the wavelength in the vicinity of 800 nm to 850 nm. Thus, in a superimposed image, a fluorescence image is superimposed with a white light image while treating the fluorescence as a G image of green color.

Figure 25:
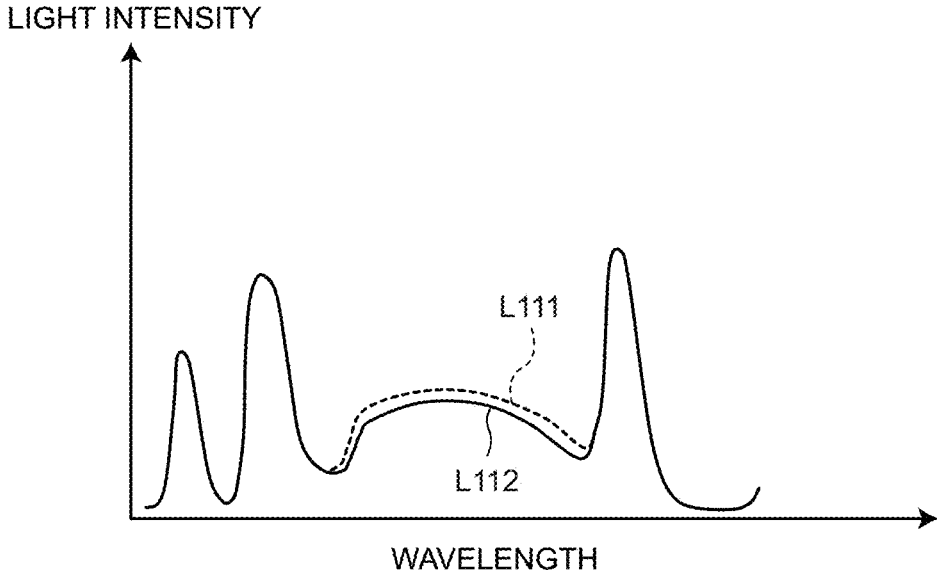
FIG. 25 is a diagram illustrating the wavelength spectrum of the post-correction white light.

FIG. 25 is a diagram illustrating the wavelength spectrum of the post-correction white light. A line L111 represents the wavelength spectrum of the pre-correction white light, and a line L112 represents the wavelength spectrum of the post-correction white light. In the post-correction white light, the G light component corresponding to the fluorescence is reduced.

Figure 26:
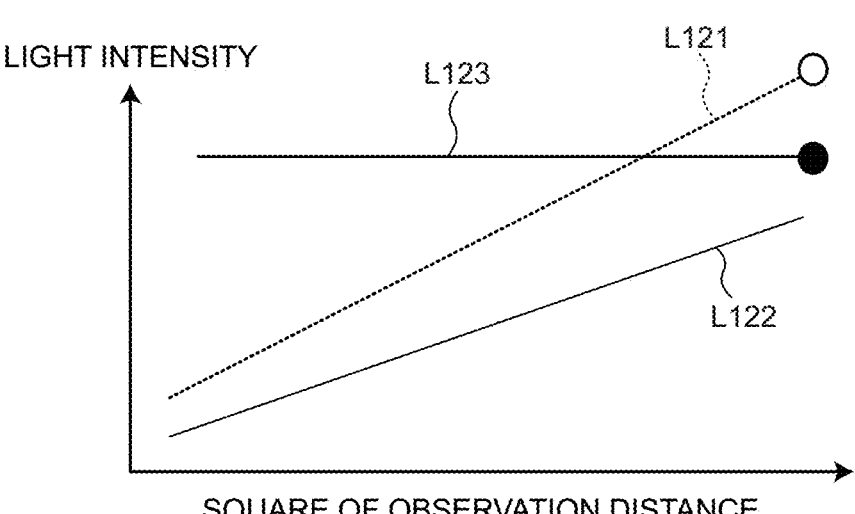
FIG. 26 is a diagram illustrating the light intensity of the G light component of the white light and the light intensity of the pumping light.

FIG. 26 is a diagram illustrating the light intensity of the G light component of the white light and the light intensity of the pumping light. A line L121 represents the light intensity of G light component of the pre-correction white light, a line L122 represents the light intensity of the G light component of the post-correction white light, and a line L123 represents the light intensity of the pumping light.

As illustrated in the line L121, the light intensity of the G light component of the pre-correction white light increases in proportion to the observation distance. On the other hand, as illustrated in the line L123, the light intensity of the pumping light is set to the upper limit light intensity regardless of the observation distance. Regarding the light intensity of the post-correction white light illustrated in the line L122, the G light component is reduced in association with the light intensity of the fluorescence. Hence, in the post-correction white light, the light intensity of only the G light component is lower as compared to the pre-correction white light.

According to the fourth embodiment described above, in a superimposed image, the color shade of the region of interest is dimmed from the white light image, thereby resulting in an enhancement in the viewability of the region of interest.

The ICG is used in achieving enhancement in the viewability of the site of lesion such as the liver. However, there are times when the bile or the fat gets captured in the background of a superimposed image. The reflected light from the bile or the fat includes components from yellow color to green color. Hence, when the region of interest is displayed in green color, there are times when the boundary between the background and the region of interest becomes obscure. In such a case, as a result of implementing the fourth embodiment, it becomes possible to achieve enhancement in the viewability of the boundary.

Fifth Embodiment

The disclosure can be implemented in the case of performing observation by irradiating the subject with narrow-band lights having two different wavelengths and the normal light.

The image generating unit 41 generates a first narrow-band light image based on an image signal captured as a result of irradiating the subject with a first narrow-band light. Moreover, the image generating unit 41 generates a second narrow-band light image based on an image signal captured as a result of irradiating the subject with a second narrow-band light.

The light source control unit 42 can control the light intensity of the first narrow-band to a value that is decided according to the brightness of the first narrow-band light image and according to a fourth ratio that is different than the first ratio, and can keep the brightness of the first narrow-band light image constant regardless of the observation distance. Moreover, when the brightness of the first narrow-band light image is equal to or greater than a threshold value, the light source control unit 42 controls the light intensity of the first narrow-band light to a first predetermined light intensity.

The first predetermined light intensity is set, for example, according to the parameters related to the first narrow-band light image. Alternatively, the first predetermined light intensity can be a predetermined value, or can be set according to the parameters related to the devices constituting the imaging element 25, or can be set according to the observation mode.

In an identical manner, the light source control unit 42 can control the light intensity of the second narrow-band light to a value that is decided according to the brightness of the second narrow-band light image and according to a fifth ratio that is different than the fourth ratio, and can keep the brightness of the second narrow-band light image constant regardless of the observation distance. Moreover, when the brightness of the second narrow-band light image is equal to or greater than a threshold value, the light source control unit 42 controls the light intensity of the first narrow-band light to a second predetermined light intensity.

The second predetermined light intensity is set, for example, to a predetermined value. Alternatively, the second predetermined light intensity can be set according to the parameters related to the second narrow-band light image, or can be set according to the parameters related to the devices constituting the imaging element 25 that performs imaging of the subject, or can be set according to the observation mode.

As a result of performing the control as explained above, in an identical manner to the first embodiment, the light intensity of the first narrow-band light and the light intensity of the second narrow-band light can be set to a high value without any correlation to the light intensity of the normal light. That enables achieving enhancement in the viewability of the first narrow-band light image and the second narrow-band light image. Moreover, when the observation distance is short, the light intensity of the first narrow-band light and the light intensity of the second narrow-band light can be set to the upper limit light intensity.

Meanwhile, assume that, according to a user operation, it is possible to switch between a first observation mode meant for observing the first narrow-band light and a second observation mode meant for observing the second narrow-band light. In that case, the light source control unit 42 can set, in the first observation mode, the first predetermined light intensity to be higher than the second predetermined light intensity; and can set, in the second observation mode, the second predetermined light intensity to be higher than the first predetermined light intensity.

Other Embodiments

In the embodiments described above, the explanation is given about performing fluorescence observation and NBI observation using the ICG. However, that is not the only possible case.

Alternatively, using protoporphyrin IX (PpIX), which is generated when 5-ALA (aminolaevulinic acid) is metabolized in the mitochondria, as the fluorescent material; if the pumping light having the wavelength of 410 nm is applied, then it becomes possible to observe red fluorescence having peaks at the wavelength of 635 nm and 705 nm.

In an identical manner, when ALM-488 is administered as parenteral infusion and when a predetermined pumping light is applied, it results in the occurrence of fluorescence in the nerve tissue. Hence, it becomes possible to perform fluorescence observation.

In an identical manner, when EMI-137 (GE-137) is administered intravenously and when near infrared rays are applied as the pumping light, it becomes possible to observe fluorescence having the peak in the wavelength band of 675 nm.

In an identical manner, when LUM-015 is administered and when LUM-015 that has been activated in a tumor and in the major surrounding is irradiated with a predetermined pumping light, it results in the occurrence of fluorescence. Hence, it becomes possible to perform fluorescence observation.

In an identical manner, when SGM-101 is injected and when a predetermined pumping light is applied, it results in the occurrence of fluorescence. Hence, it becomes possible to perform fluorescence observation.

In an identical manner, when AVB-620 is injected intravenously before the surgery of a breast cancer patient and when a predetermined pumping light is applied, it results in the occurrence of fluorescence. Hence, it becomes possible to perform fluorescence observation.

In an identical manner, when OTL-38 is given by the IV route and when a pumping light having the wavelength in the vicinity of 780 nm is applied, it results in the occurrence of fluorescence. Hence, it becomes possible to perform fluorescence observation.

In an identical manner, using IRDye-800, fluorescence observation can be performed with the use of the pumping light having the wavelength of 780 nm.

In such fluorescence observation, if the light intensity of the pumping light is controlled using the second ratio, then the light intensity of the pumping light can be set to a high value without any correlation to the light intensity of the white light. That enables achieving enhancement in the viewability of the fluorescence images. Moreover, when the brightness of the fluorescence images is equal to or greater than a threshold value, the light intensity of the pumping light can be set to the upper limit light intensity.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

According to the disclosure, it becomes possible to provide a control device that enables achieving enhancement in the viewability of a narrow-band light image generated during the observation performed using a narrow-band light.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control device comprising:
   one or more processors comprising hardware, the one or more processors being configured to:
   generate a white light image based on a first image signal captured as a result of irradiating a subject with a white light;
   generate a first narrow-band light image based on a second image signal captured as a result of irradiating the subject with a first narrow-band light;
   generate a second narrow-band light image based on a third image signal captured as a result of irradiating the subject with a second narrow-band light, control a light intensity of the white light to a first value which is determined according to brightness of the white light image and according to a first ratio, wherein:

when brightness of the first narrow-band light image is equal to or greater than a threshold value, the one or more processors being configured to control a light intensity of the first narrow-band light to be equal to a first predetermined light intensity, and when brightness of the second narrow-band light image is equal to or greater than a threshold value, the one or more processors being configured to control a light intensity of the second narrow-band light to be equal to a second predetermined light intensity.

2. The control device according to claim 1, wherein the one or more processors being configured to control the light intensity of the white light such that the brightness of a normal light image becomes constant.

3. The control device according to claim 1, wherein the first predetermined light intensity and second predetermined light intensity is set according to a predetermined value, a parameter related to the narrow-band light image, a parameter related to a device comprising an image sensor configured to perform imaging of the subject, an observation mode, or observation distance.

4. The control device according to claim 1, wherein the first predetermined light intensity is set according to a parameter related to the first narrow-band light image, and the second predetermined light intensity is set to a predetermined value.

5. The control device according to claim 1, wherein in a first observation mode, the one or more processors being configured to set the first predetermined light intensity to be greater than the second predetermined light intensity, and in a second observation mode, the one or more processors being configured to set the second predetermined light intensity to be greater than the first predetermined light intensity.

6. The control device according to claim 5, wherein the first observation mode and the second observation mode are switchable according to a user operation.

7. The control device according to claim 1, wherein the one or more processors being configured to generate an image obtained by performing a gain correction with respect to the narrow-band light image such that the brightness of the narrow-band light image is equal to a predetermined value.

8. The control device according to claim 1, wherein the one or more processors being configured to generate an image obtained by performing a gain correction with respect to the narrow-band light image such that the brightness of the narrow-band light image is equal to or greater than a predetermined value.

9. The control device according to claim 7, wherein the one or more processors being configured to set a gain with respect to the narrow-band light to a third value which is determined according to the brightness of the narrow-band light image and according to a third ratio.

10. The control device according to claim 9, wherein the one or more processors being configured to set a gain with respect to the white light image and a gain with respect to the narrow-band light image such that a ratio between the brightness of the white light image and the brightness of the narrow-band light image becomes substantially constant.

11. The control device according to claim 1, wherein the one or more processors being configured to generate a superimposed image by superimposing the white light image and one of the first narrow-band light image or second narrow-band light image.

12. The control device according to claim 11, wherein the one or more processors being configured to generate the superimposed image by correcting color balance of the white light image such that there is a decrease in a component corresponding to the narrow-band light in the superimposed image.

13. The control device according to claim 12, wherein the one or more processors being configured to generate the superimposed image by adjusting color balance of the white light image such that a maximum contrast is achieved between a region of interest in the narrow-band light image and background other than the region of interest.

14. The control device according to claim 12, wherein the one or more processors being configured to correct the color balance of the white light image such that background of the superimposed image has a same color shade as a color shade of background of the white light image.

15. The control device according to claim 11, wherein the one or more processors being configured to correct light intensity balance of the white light such that there is a decrease in a component corresponding to the narrow-band light in the superimposed image.

16. The control device according to claim 15, wherein the one or more processors being configured to correct the light intensity balance of the white light image such that a maximum contrast is achieved between a region of interest in the narrow-band light image and background other than the region of interest.

17. The control device according to claim 15, wherein the one or more processors is configured to correct the light intensity balance of the white light such that background of the superimposed image has a same color shade as a color shade of background of the normal light image.

18. An endoscope system comprising:

the control device according to claim 1;

a light source device configured to irradiate the normal light and the narrow-band light; and an endoscope configured to output first and second signals.

* * * * *